US008420800B2

(12) United States Patent
Zama et al.

(10) Patent No.: US 8,420,800 B2
(45) Date of Patent: Apr. 16, 2013

(54) HEAD-AND-NECK TUMOR PROLIFERATION INHIBITOR

(75) Inventors: Takeru Zama, Tokyo (JP); Koichiro Saito, Tokyo (JP); Akira Hirasawa, Tokyo (JP); Koji Inagaki, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 13/263,800

(22) PCT Filed: Apr. 16, 2010

(86) PCT No.: PCT/JP2010/002764
§ 371 (c)(1),
(2), (4) Date: Dec. 12, 2011

(87) PCT Pub. No.: WO2010/119698
PCT Pub. Date: Oct. 21, 2010

(65) Prior Publication Data
US 2012/0088816 A1   Apr. 12, 2012

(30) Foreign Application Priority Data

Apr. 16, 2009  (JP) ................... 2009-099861
Jun. 11, 2009  (JP) ................... 2009-140088
Nov. 27, 2009  (JP) ................... 2009-270157

(51) Int. Cl.
*C07H 21/04* (2006.01)
*C07H 21/02* (2006.01)
*A61K 48/00* (2006.01)

(52) U.S. Cl.
USPC ......... 536/24.5; 514/44; 536/23.1; 536/24.3; 536/24.31; 536/24.33

(58) Field of Classification Search ......... None
See application file for complete search history.

(56) References Cited

FOREIGN PATENT DOCUMENTS

| JP | 2008-239596 | 10/2008 |
| JP | 2009-171876 | 8/2009 |
| WO | WO 2007/081740 | 7/2007 |
| WO | WO 2008/094545 A2 | 8/2008 |
| WO | WO 2009/150839 A1 | 12/2009 |
| WO | WO 2010/050328 A1 | 5/2010 |

OTHER PUBLICATIONS

Barbarotto et al., "MicroRNAs and Cancer: Profile, profile, profile," Int. J. Cancer, 122, pp. 969-977, 2008.
Hiyoshi et al., "MicroRNA-21 Regulates the Proliferation and Invasion in Esophageal Squamous Cell Carcinoma," Clin Cancer Res., 15(6), pp. 1915-1922, Mar. 15, 2009.
Kozaki et al., "Identification of Tumor Suppressor MicroRNA Silenced by DNA Methylation in Oral Squamous Cell Carcinoma," Retrieved from Internet Site http://medproc.tokyojst.go.jp/yokou/disp/JYDetailJd2jsp:jsessionid=006ECC6901FC5C6BD0C5F . . . On Jun. 22, 2010, vol. 66, p. 419, Aug. 25, 2007.
Marur et al., "Head and Neck Cancer: Changing Epidemiology, Diagnosis and Treatment," Mayo Clinic Proceedings, 83(4), pp. 489-501, Apr. 2008.
Tran et al., "MicroRNA Expression Profiles in Head and Neck Cancer Cell Lines," Biochemical Biophysical Research Communications, 358(1), pp. 12-17, Apr. 9, 2007.
Zeng et al., "MicroRNAs and Small Interfering RNAs Can Inhibit mRNA Expression by Similar Mechanisms," PNAS, 100(17), pp. 9779-9784, Aug. 19, 2003.
Oshima et al., "Cancer/Statistics White Paper, Disease/Death/Prognosis," Shinohara Shuppannsha Inc., 2004 with English translation.

*Primary Examiner* — Amy Bowman
(74) *Attorney, Agent, or Firm* — Kenneth H. Sonnenfeld; Margaret B. Brivanlou; King & Spalding

(57) ABSTRACT

It is to provide a novel head-and-neck tumor proliferation inhibitor, head-and-neck tumor metastasis inhibitor and pharmaceutical composition for treating a head-and-neck tumor. The present invention is characterized by using an inhibitory substance of a microRNA whose expression increases in a head-and-neck tumor and/or a promoting substance of a microRNA whose expression decreases in a head-and-neck tumor. Preferred examples of the microRNA whose expression increases in a head-and-neck tumor include miR-455-3p, miR-455-5p, miR-130b, miR-130b*, miR-801, miR-196a, miR-21 and miR-31. Preferred examples of the microRNA whose expression decreases in a head-and-neck tumor include miR-133b, miR-145 and miR-375.

2 Claims, 5 Drawing Sheets

HEAD-AND-NECK TUMOR PROLIFERATION INHIBITOR

TECHNICAL FIELD

The present invention generally relates to the fields of cell biology and molecular biology. More specifically, the present invention relates to a head-and-neck tumor proliferation inhibitor, head-and-neck tumor metastasis inhibitor and pharmaceutical composition for treating a head-and-neck tumor containing an inhibitory substance of a microRNA (miRNA) whose expression increases in a head-and-neck tumor and/or a promoting substance of a microRNA whose expression decreases in a head-and-neck tumor.

BACKGROUND ART

The head-and-neck tumor is a tumor developing in e.g., the ears, nose, pharynx, larynx, cervical region or oral cavity. In particular, a malignant tumor thereof is mostly found in males of 50 years old or older and represents 6% of all malignant tumors. The morbidity increases with age and 650,000 or more people are afflicted over the world and 350,000 of them die of the disease (malignant tumor). Among them, larynx cancer is a malignant tumor most commonly developed in the head and neck. The future forecast of annual death tolls estimates that the number of deaths will increase (see Non-patent Document 1).

A head-and-neck tumor is diagnosed based on staging performed using endoscopic inspection and various image inspections (CT, MRI, PET, etc.) and tissue diagnosis by means of biopsy. In the case of a benign tumor diagnosed based on these, a primary radical resection enabling a complete cure is performed; whereas, in the case of a malignant tumor, an operation, radiation therapy and chemotherapy are performed. In the case of advanced cancer, a combination therapy of them must be required. However, an operation for a head-and-neck tumor gives significant cosmetic damage to the head and neck and the face, and in addition, highly affects physical functions such as vocalization and swallowing. Because of significant physical and psychological invasion, patient's QOL (Quality of Life) significantly decreases. In addition, a therapeutic effect of combination therapies of these is not always high and thus a 5-year survival rate in advanced cancer remains at most about 30% (see Non-patent Document 2).

MicroRNA is a single-stranded RNA having a length of about 22 bases, present within a cell and not translated into a protein (see Non-patent Document 3). MicroRNA was found in C. elegans in 1993, also in a vertebrate animal in 2001 and conserved beyond species. At present, it is estimated that nearly 1000 microRNAs are present on a human genome and so far 800 or more human microRNAs have been cloned. Furthermore, microRNA presumably controls a gene by binding to mRNA in 30% of the protein coding region on a genome (see Non-patent Document 4). Therefore, functional destruction of microRNA may cause various diseases. From the above facts, recently genetic diagnosis, determination of disease types, prognostic prediction or development of pharmaceutical products using microRNA has been expected. In Europe and the United States, functional analysis of microRNA and application of microRNA to medical services have been tried. Furthermore, with respect to cancer and a malignant tumor, involvement of a cancer gene and a cancer suppressor gene in onset and progress thereof is known but involvement of microRNA in control thereof is also elucidated. MicroRNA is regarded to be involved in controlling all of expression, progress and metastasis of a tumor. There are some reports on development of a medicinal drug of a microRNA (for example, colon cancer cell proliferation inhibitor using miR-34; see Patent Document 1) using these; however, at present, the development thereof is extremely slow.

PRIOR ART DOCUMENTS

Patent Document
 Patent Document 1: Japanese Unexamined Patent Application Publication No. 2008-239596
Non-Patent Documents
 Non-patent Document 1: "Cancer white paper", Akira Oshima, et al., issued in June 2004, Shinoharashinsha Inc.
 Non-patent Document 2: Marur S, Forastiere A A. Head and neck cancer: changing epidemiology, diagnosis, and treatment. Mayo Clin Proc. 2008; 83(4): 489-501.
 Non-patent Document 3: Barbarotto E, Schmittgen T D, Calin G A. microRNAs and cancer: profile, profile, profile. Int J Cancer. 2008; 122(5): 969-977.
 Non-patent Document 4: Zeng Y, Yi R, Cullen BR. miRNAs and small interfering RNAs can inhibit mRNA expression by similar mechanisms. Proc Nat Acad Sci 2003; 100: 9779-9784.

SUMMARY OF THE INVENTION

Object to be Solved by the Invention

An object of the present invention is to provide a novel head-and-neck tumor proliferation inhibitor, head-and-neck tumor metastasis inhibitor and pharmaceutical composition for treating a head-and-neck tumor.

Means to Solve the Object

The present inventors, up to present, have already constructed a microRNA expression profile in the larynx tissue with a view to clarifying a microRNA specifically expressed in the tissue of larynx cancer, which is one of head-and-neck tumors (see Japanese Patent Application No. 2008-243306). As a result, they found microRNAs, having a tendency of specifically expressing in the tissue of larynx cancer, compared to a non-cancer portion of the larynx such as a normal tissue or an inflammation tissue. Of them, miR-196a was confirmed whose expression particularly significantly increases compared to that in a non-cancer portion, and miR-133b and miR-375 were confirmed whose expression particularly significantly decreases compared to that in a non-cancer portion. Then, they considered that these microRNAs are used as novel therapeutic molecular targets for a head-and-neck tumor including larynx cancer and attempted to analyze for biological significance of the microRNAs by using larynx cancer cells, JHU-011, which was an established head-and-neck cancer cell-line, as well as two types of cancer cell-lines (Ca9-22: oral cancer, SAS: tongue cancer), which are stratified squamous epithelium cancer cells of the head and neck.

Prior to this analysis, first, the expression levels of the aforementioned three types of microRNAs were checked in Ca9-22 and SAS in comparison with those in a non-cancer tissue of the larynx which serve as a control (see Reference Example 1 described later). As a result, the expression level of miR-196a in Ca9-22 was about 65 times as high as that of the control; whereas the expression level of miR-133b was about 1/64 as low as that of the control. Furthermore, as to miR-375, expression was not confirmed. Similarly, in SAS, the expression level of miR-196a was also about 88 times as high as that of the control; whereas the expression levels of miR-133b and miR-375 were about 1/19 and about 1/148, respectively, as low as that of the control. In short, it was confirmed that miR-196a is a microRNA whose expression increases in a head-and-neck tumor; whereas miR-133b and miR-375 are microRNAs whose expression decreases in a head-and-neck tumor.

Then, the present inventors introduced an inhibitory substance of miR-196a (microRNA whose expression increases in a head-and-neck tumor) and mimetic substances of miR-133b and miR-375 (microRNAs whose expression decreases in a head-and-neck tumor) to four types of head-and-neck cancer cell-lines in total including the aforementioned three types of head-and-neck cancer cell-lines and FaDu cells (lower pharynx cancer cell-line). As a result, they found that proliferation of the above four types of head-and-neck cancer cells is inhibited. In addition, they administered an miR-196a inhibitory substance to head-and-neck tumor model mice. As a result, they found that e.g., growth and metastasis of the tumor are inhibited. Based on the findings, the present invention was accomplished.

More specifically, the present invention relates to (1) a pharmaceutical composition for treating a head-and-neck tumor, containing an inhibitory substance of a microRNA whose expression increases in a head-and-neck tumor and/or a promoting substance of a microRNA whose expression decreases in a head-and-neck tumor, (2) a head-and-neck tumor proliferation inhibitor containing an inhibitory substance of a microRNA whose expression increases in a head-and-neck tumor and/or a promoting substance of a microRNA whose expression decreases in a head-and-neck tumor, (3) the head-and-neck tumor proliferation inhibitor according to the above (2), wherein the inhibitory substance of a microRNA whose expression increases in a head-and-neck tumor is an antisense nucleic acid of the microRNA whose expression increases in a head-and-neck tumor, (4) the head-and-neck tumor proliferation inhibitor according to the above (2) or (3), wherein the promoting substance of a microRNA whose expression decreases in a head-and-neck tumor is a mimetic substance of the microRNA whose expression decreases in a head-and-neck tumor, (5) the head-and-neck tumor proliferation inhibitor according to any one of the above (2) to (4), wherein the microRNA whose expression increases in a head-and-neck tumor is one or more microRNAs selected from the group of microRNAs consisting of miR-455-3p, miR-455-5p, miR-130b, miR-130b*, miR-801, miR-196a, miR-21 and miR-31, and the microRNA whose expression decreases in a head-and-neck tumor is one or more microRNAs selected from the group of microRNAs consisting of miR-133b, miR-145 and miR-375.

Furthermore, the present invention relates to (6) a head-and-neck tumor metastasis inhibitor containing an inhibitory substance of a microRNA whose expression increases in a head-and-neck tumor and/or a promoting substance of a microRNA whose expression decreases in a head-and-neck tumor, (7) the head-and-neck tumor metastasis inhibitor according to the above (6), wherein the inhibitory substance of a microRNA whose expression increases in a head-and-neck tumor is an antisense nucleic acid of the microRNA whose expression increases in a head-and-neck tumor, (8) the head-and-neck tumor metastasis inhibitor according to the above (6) or (7), wherein the promoting substance of a microRNA whose expression decreases in a head-and-neck tumor is a mimetic substance of the microRNA whose expression decreases in a head-and-neck tumor, (9) the head-and-neck tumor metastasis inhibitor according to any one of the above (6) to (8), wherein the microRNA whose expression increases in a head-and-neck tumor is one or more microRNAs selected from the group of microRNAs consisting of miR-455-3p, miR-455-5p, miR-130b, miR-130b*, miR-801, miR-196a, miR-21 and miR-31, and the microRNA whose expression decreases in a head-and-neck tumor is one or more microRNAs selected from the group of microRNAs consisting of miR-133b, miR-145 and miR-375.

EFFECT OF THE INVENTION

According to the present invention, it is possible to provide e.g., a head-and-neck tumor proliferation inhibitor having a proliferation inhibitory effect on a head-and-neck tumor, a head-and-neck tumor metastasis inhibitor having a metastasis inhibitory effect on a head-and-neck tumor, and a pharmaceutical composition for treating a head-and-neck tumor.

BRIEF DESCRIPTION OF DRAWINGS

FIG. 1
FIG. 1A: The measurement results of the number of JHU-011 cells, which were transfected with INH NC (negative control) or INH 196a (RNA composed of an antisense sequence of miR-196a), cultured, and then measured on 3rd day and 5th day of the culturing. Note that the graph plotted by open-circle dots shows the results of INH NC; whereas the graph plotted by solid-circle dots shows the results of INH 196a.

FIG. 1B, the left panel: A graph showing relative activity of a protease derived from viable JHU-011 cells, which were transfected with INH NC or INH 196a and cultured for 3 days. Note that the left bar graph in the panel shows the result of the INH NC group; whereas the right bar graph shows the result of the INH 196a group.

FIG. 1B, the right panel: A graph showing relative activity of a protease derived from dead JHU-011 cells, which were transfected with INH NC or INH 196a and cultured for 3 days. Note that the left bar graph in the panel shows the result of the INH NC group; whereas the right bar graph shows the result of the INH 196a group.

FIG. 1C, the left panel: A fluorescence micrograph showing the state of JHU-011 cells, which were transfected with INH NC, cultured for 3 days and subjected to Hoechst staining.

FIG. 1C, the right panel: A fluorescence micrograph showing the state of JHU-011 cells, which were transfected with INH 196a, cultured for 3 days and subjected to Hoechst staining.

FIG. 2, the right panel: A fluorescence micrograph showing the state of JHU-011 cells, which were transfected with MIM 375 (a mimetic gene of miR-375), cultured for 5 days and subjected to Hoechst staining.

FIG. 3
FIG. 3A, the left panel: A photograph showing appearance of a tumor of a mouse group, which were grafted with a cancer cell and administered with INH NC in 9 weeks after the grafting. In the photograph, a grown tumor with necrosis is observed at the center.

FIG. 3A, the right panel: A photograph showing appearance of a tumor of a mouse group, which were grafted with a cancer cell and administered with INH 196a in 9 weeks after the grafting.

FIG. 3B: A graph showing a change of the relative tumor volume (%) of head-and-neck tumor model mouse groups administered with INH 196a or INH NC. Note that the relative tumor volume (%) herein refers to an average of tumor volume (%) relative to the average tumor volume in one week after the grafting of a cancer cell to mice, regarded as 100% in each group. Furthermore, the graph plotted by open-circle dots shows the result of the INH NC group; whereas the graph plotted by solid-circle dots shows the result of INH 196a.

FIG. 4

Photographs showing the results of tissue slices, which were prepared from tumor tissues of both head-and-neck tumor model mouse groups (3 months after grafting) in the experiment of FIG. 3 and subjected to hematoxylin/eosin staining (HE staining). FIGS. 4A and B show the results of the INH 196a administration group; whereas FIGS. 4C and D show the results of the INH NC administration group.

FIG. 5

FIGS. 5A and B show the results of the INH 196a administration group; whereas FIGS. 5C and D show the results of the INH NC administration group.

MODE OF CARRYING OUT THE INVENTION

The pharmaceutical composition for treating a head-and-neck tumor, head-and-neck tumor proliferation inhibitor and head-and-neck tumor metastasis inhibitor of the present invention are not particularly limited as long as they contain an inhibitory substance of a microRNA whose expression increases in a head-and-neck tumor (hereinafter, also referred to as the "inhibitory substance of the present invention") and/or a promoting substance of a microRNA whose expression decreases in a head-and-neck tumor (hereinafter, also referred to as the "promoting substance of the present invention"). Preferred examples of the aforementioned "microRNA whose expression increases in a head-and-neck tumor" include miR-455-3p (microRNA-455-3p) (SEQ ID NO:1), miR-455-5p (microRNA-455-5p) (SEQ ID NO:2), miR-130b (microRNA-130b) (SEQ ID NO:3), miR-130b* (microRNA-130b*) (SEQ ID NO:4), miR-801 (microRNA-801) (SEQ ID NO:5), miR-196a (microRNA-196a) (SEQ ID NO:6), miR-21 (microRNA-21) (SEQ ID NO:7) and miR-31 (microRNA-31) (SEQ ID NO:8). Of them, miR-196a can be more preferably mentioned. Preferred examples of the aforementioned "microRNA whose expression decreases in a head-and-neck tumor" include miR-133b (microRNA-133b) (SEQ ID NO:9), miR-145 (microRNA-145) (SEQ ID NO:10) and miR-375 (microRNA-375) (SEQ ID NO:11). Of them, miR-133b and miR-375 can be more preferably mentioned. As is apparent from the results of Examples described later, since the inhibitory substance and promoting substance of the present invention have a growth inhibitory effect and a metastasis inhibitory effect on a head-and-neck tumor, they can be used as a pharmaceutical composition for treating a head-and-neck tumor, a head-and-neck tumor proliferation inhibitor and a head-and-neck tumor metastasis inhibitor. The fact that expression of miR-455-3p, miR-455-5p, miR-130b, miR-130b*, miR-801, miR-196a, miR-21 and miR-31 increases in a head-and-neck tumor and the fact that expression of miR-133b, miR-145 and miR-375 decreases in a head-and-neck tumor are also disclosed in Japanese Patent Application No. 2008-243306 mentioned above.

The "microRNA whose expression increases in a head-and-neck tumor" refers to a microRNA whose expression increases in a head-and-neck tumor, compared to that in a non-cancer tissue such as a normal tissue of the head and neck. The "microRNA whose expression decreases in a head-and-neck tumor" refers to a microRNA whose expression decreases in a head-and-neck tumor, compared to that in a non-cancer tissue such as a normal tissue of the head and neck. Whether the expression of a specific microRNA increases or decreases in a head-and-neck tumor compared to that in a non-cancer tissue such as a normal tissue of the head and neck can be checked by a method (microarray method and quantitative PCR method) disclosed in Reference Example 1 described later and the specification of Japanese Patent Application No. 2008-243306 as described above. Furthermore, the "microRNA whose expression increases in a head-and-neck tumor" herein is preferably a "microRNA whose expression increases specifically in a head-and-neck tumor". The "microRNA whose expression decreases in a head-and-neck tumor" herein is preferably a "microRNA whose expression decreases specifically in a head-and-neck tumor".

Furthermore, the "inhibitory substance of a microRNA whose expression increases in a head-and-neck tumor" refers to a substance which inhibits the action of the microRNA by directly or indirectly binding to the microRNA, or directly or indirectly decomposing the microRNA. Preferred examples of the inhibitory substance of the present invention include substances, which inhibit the action of the microRNA by directly binding to the microRNA whose expression increases in a head-and-neck tumor. Of them, nucleic acids, which inhibit the action of the microRNA by directly binding to the microRNA whose expression increases in a head-and-neck tumor, are preferably mentioned. Of them, antisense nucleic acids to the microRNA are more preferably mentioned. Of them, antisense DNAs and RNAs to the microRNA are further preferably mentioned. Of them, RNA (antisense RNA of miR-455-3p) consisting of an antisense sequence to the sequence represented by SEQ ID NO:1, RNA (antisense RNA of miR-455-5p) consisting of an antisense sequence to the sequence represented by SEQ ID NO:2, RNA (antisense RNA of miR-130b) consisting of an antisense sequence to the sequence represented by SEQ ID NO:3, RNA (antisense RNA of miR-130b*) consisting of an antisense sequence to the sequence represented by SEQ ID NO:4, RNA (antisense RNA of miR-801) consisting of an antisense sequence to the sequence represented by SEQ ID NO:5, RNA (antisense RNA of miR-196a) consisting of an antisense sequence to the sequence represented by SEQ ID NO:6, RNA (antisense RNA of miR-21) consisting of an antisense sequence to the sequence represented by SEQ ID NO:7 and RNA (antisense RNA of miR-31) consisting of an antisense sequence to the sequence represented by SEQ ID NO:8 are further more preferably mentioned. Of them, the antisense RNA of miR-196a is particularly preferably mentioned. As the inhibitory substance of the present invention, an inhibitory substance of one microRNA whose expression increases in a head-and-neck tumor may be used alone; however, in view of more reliably and more sufficiently obtaining a head-and-neck tumor proliferation inhibitory effect and a head-and-neck tumor metastasis inhibitory effect, it is preferred to use inhibitory substances of two or more microRNAs whose expression increases in a head-and-neck tumor, in combination. Furthermore, the inhibitory substance of a microRNA to be used in a head-and-neck tumor proliferation inhibitor focusing on a head-and-neck tumor proliferation inhibitory effect may differ from that to be used in a head-and-neck tumor metastasis inhibitor focusing on a head-and-neck tumor metastasis inhibitory effect.

The "substance inhibiting the action of a microRNA" can be determined by, for example, proliferation assay of a head-and-neck squamous epithelium cancer cell-line in Example 1 described later, based on whether a cell proliferation inhibitory effect is observed or not when the substance is introduced into any one of head-and-neck squamous epithelium cancer cell-lines by, e.g., transfection, and determined by in-vivo growth assay using a head-and-neck tumor model mouse in Example 2 described later, based on whether a tumor proliferation inhibitory effect is observed or not when the substance is inoculated in a tumor formation portion of a head-and-neck tumor model mouse.

The "promoting substance of a microRNA whose expression decreases in a head-and-neck tumor" refers to a substance which accelerates the action of the microRNA by directly or indirectly binding to the microRNA or a mimetic substance of the microRNA. The mimetic substance of the microRNA refers to a substance containing an RNA having a nucleotide sequence which has deletion, substitution, or addition of one or more nucleotides in the nucleotide sequence of the microRNA, and having a head-and-neck tumor proliferation inhibitory effect and a head-and-neck tumor metastasis inhibitory effect, and, for convenience sake, a substance containing the microRNA whose expression decreases in a head-and-neck tumor, itself. Preferred examples of the promoting substance of the present invention include mimetic substances of the microRNA whose expression decreases in a head-and-neck tumor. Of them, nucleic acids, which mimic the microRNA whose expression decreases in a head-and-neck tumor, can be preferably mentioned. Of them, substances containing such RNA itself can be more preferably mentioned. Of them, double-stranded RNAs consisting of such RNA and the complementary sequence of the RNA can be further preferably mentioned. Of them, a double-stranded RNA consisting of miR-133b RNA sequence (SEQ ID NO:9) and the complementary sequence of the RNA sequence, a double-stranded RNA consisting of miR-145 RNA sequence (SEQ ID NO:10) and the complementary sequence of the RNA sequence, and a double-stranded RNA consisting of miR-375 RNA sequence (SEQ ID NO:11) and the complementary sequence of the RNA sequence can be further more preferably mentioned. Of them, a double-stranded RNA consisting of miR-375 RNA sequence and the complementary sequence of the RNA sequence can be particularly preferably mentioned. As the promoting substance of the present invention, a promoting substance of a microRNA whose expression decreases in a head-and-neck tumor may be used alone; however, in view of more reliably and more sufficiently obtaining a head-and-neck tumor proliferation inhibitory effect and a head-and-neck tumor metastasis inhibitory effect, it is preferred to use inhibitory substances of two or more microRNAs whose expression decreases in a head-and-neck tumor, in combination. Furthermore, the promoting substance of a microRNA to be used in a head-and-neck tumor proliferation inhibitor focusing on a head-and-neck tumor proliferation inhibitory effect may differ from that to be used in a head-and-neck tumor metastasis inhibitor focusing on a head-and-neck tumor metastasis inhibitory effect.

The level of the head-and-neck tumor proliferation inhibitory effect of the inhibitory substance and promoting substance of the present invention is not particularly limited; however, in the proliferation assay of a head-and-neck squamous epithelium cancer cell-line in Example 1 described later, a cell proliferation inhibitory effect can be 10% or more, preferably 20% or more, more preferably 30% or more and further preferably 40% or more in one of the head-and-neck squamous epithelium cancer cell-lines. Furthermore, in in-vivo growth assay in Example 2 described later using head-and-neck tumor model mice, a head-and-neck tumor proliferation inhibitory effect, which is expressed by a proportion of the relative tumor volume (%) to the relative tumor volume (%) of a negative control administration group, in 12 weeks after cancer-cell grafting, can be 50% or less, preferably 35% or less, more preferably 25% or less and further preferably 20% or less. Furthermore, the level of the head-and-neck tumor metastasis inhibitory effect of the inhibitory substance and promoting substance of the present invention is not particularly limited; however, in pathological observation of a lymph node tissue in Example described later, a head-and-neck tumor metastasis inhibitory effect to the extent that metastasis to the cervical lymph node does not occur is preferably mentioned.

Preferred examples of the organism, from which a microRNA of the specification is derived, include mammals such as a human, a mouse, a rat, a hamster, a guinea pig, a monkey, a cow, a pig, a horse, a rabbit, a sheep, a goat, a cat and a dog. Of them, a human and a mouse can be more preferably mentioned, and particularly preferably, a human is mentioned. The microRNA sequences of SEQ ID NOs:1 to 11 are all derived from a human. Furthermore, microRNA sequences are highly conserved particularly between mammals. The microRNAs are considered to exhibit the same expression profile as in a human also in mammals other than a human. Furthermore, a microRNA sequence derived from organisms other than a human can be confirmed or specified based on the information registered in the database of the GenBank, etc.

Furthermore, the "microRNA whose expression increases in a head-and-neck tumor" in the specification includes a microRNA, which consists of an RNA having a nucleotide sequence having deletion, substitution, or addition of one or more nucleotides in the nucleotide sequence of the microRNA and whose expression increases in a head-and-neck tumor compared to that in a non-cancer tissue such as a normal tissue of the head and neck, for convenience sake. Furthermore, the "microRNA whose expression decreases in a head-and-neck tumor" in the specification includes a microRNA, which consists of an RNA having a nucleotide sequence which has deletion, substitution, or addition of one or more nucleotides in the nucleotide sequence of the microRNA and whose expression decreases in a head-and-neck tumor compared to that in a non-cancer tissue such as a normal tissue of the head and neck, for convenience sake. The number of the "one or more" mentioned above is preferably 1 to 5, more preferably 1 to 3, particularly preferably 1 to 2 and further preferably 1. Whether the expression of the RNA consisting of a nucleotide sequence having a deletion, etc., increases or decreases in the head-and-neck tumor tissue compared to that in a non-cancer tissue such as a normal tissue of the head and neck can be easily confirmed by, for example, a microarray method and quantitative PCR method described later.

As long as the head-and-neck tumor proliferation inhibitor of the present invention has a desired head-and-neck tumor proliferation inhibitory effect, the inhibitor may contain an optional component such as another head-and-neck tumor proliferation inhibitor and an anticancer agent other than the inhibitory substance and/or promoting substance of the present invention. Furthermore, as long as the head-and-neck tumor metastasis inhibitor has a desired head-and-neck tumor metastasis inhibitory effect, the inhibitor may contain an optional component such as another head-and-neck tumor metastasis inhibitor other than the inhibitory substance and/or promoting substance of the present invention. Furthermore, as long as the pharmaceutical composition for treating a head-and-neck tumor has a desired head-and-neck tumor proliferation inhibitory effect and/or head-and-neck tumor metastasis inhibitory effect, the composition may contain an optional component such as another head-and-neck tumor proliferation inhibitor, an anticancer agent and a head-and-neck tumor metastasis inhibitor other than the inhibitory substance and/or promoting substance of the present invention. The head-and-neck tumor proliferation inhibitor, head-and-neck tumor metastasis inhibitor and pharmaceutical composition for treating a head-and-neck tumor of the present invention may contain both the inhibitory substance of the present invention and the promoting substance of the present invention. Furthermore, the pharmaceutical composition for treating a head-and-neck tumor preferably contains the inhibitory substance of the present invention and/or the promoting substance of the present invention excellent in the head-and-neck tumor proliferation inhibitory effect in combination with the inhibitory substance of the present invention and/or the promoting substance of the present invention excellent in the head-and-neck tumor metastasis inhibitory effect, in view of obtaining more excellent head-and-neck tumor therapy effect.

The inhibitory substance and promoting substance of the present invention contained in the head-and-neck tumor proliferation inhibitor, head-and-neck tumor metastasis inhibitor and pharmaceutical composition for treating a head-and-neck tumor of the present invention can be formed into an appropriate preparation by a customary method. The dosage form of the preparation may be a solid preparation such as a powder and a granule; however, a liquid, such as a solution, an emulsion and a suspension, is preferred in view of obtaining an excellent head-and-neck tumor proliferation inhibitory effect and head-and-neck tumor metastasis inhibitory effect. As a method for producing the liquid formulation, preferably a method of mixing the inhibitory substance and promoting substance of the present invention with a solvent, and further preferably, a method of mixing them with a suspending agent and an emulsifier can be mentioned. As described above, in the case where the inhibitory substance and promoting substance of the present invention are each formed into a preparation, if necessary, in forming a preparation, an appropriate pharmaceutically acceptable carrier component such as an excipient, a binder, a solvent, a solubilization agent, a suspending agent, an emulsifier, an isotonic agent, a buffer, a stabilizer, a soothing agent, an antiseptic agent, antioxidant, a colorant, a lubricant, a disintegrator, a moisturizing agent, an adsorption agent, a sweetener and a diluent, may be optionally blended.

Furthermore, in the case where the inhibitory substance and promoting substance of the present invention are each a nucleic acid, particularly, an antisense RNA and a double-stranded RNA, a carrier for a nucleic acid such as RNA is preferably used. As such a carrier, atelocollagen (see Patent Document 1 above) and a cholesterol molecule (see NATURE, Vol 438, 1 Dec. 2005, p685-689; NATURE, Vol 452, 17, April 2008, p896-900) can be preferably mentioned. If the inhibitory substance and promoting substance of the present invention are, e.g., intravenously injected by use of these carriers, the inhibitory substance and promoting substance of the present invention can be delivered into a cell of a head-and-neck tumor tissue.

An administration method for the head-and-neck tumor proliferation inhibitor, head-and-neck tumor metastasis inhibitor and pharmaceutical composition for treating a head-and-neck tumor of the present invention is not particularly limited, as long as a desired head-and-neck tumor proliferation inhibitory effect and a desired head-and-neck tumor metastasis inhibitory effect can be obtained. For example, administration by intravenous injection and administration by injection to a head-and-neck tumor portion or a peripheral portion thereof can be mentioned. Furthermore, dose, administration times and administration concentration of the head-and-neck tumor proliferation inhibitor, head-and-neck tumor metastasis inhibitor and pharmaceutical composition for treating a head-and-neck tumor of the present invention can be appropriately controlled depending upon e.g., the state of a head-and-neck tumor of a subject and the weight of a subject.

As the type of "head-and-neck tumor" of the specification, head-and-neck cancer (initial or recurrence), head-and-neck metaplasia and head-and-neck polyp, preferably, head-and-neck cancer (initial or recurrence) and head-and-neck metaplasia, more preferably, head-and-neck cancer (initial or recurrence), and further preferably, initial head-and-neck cancer can be mentioned. Furthermore, as the head and neck of the head-and-neck tumor of the specification, head portions such as the lip, oral cavity, nose, paranasal cavity, saliva gland, ear, temporal bone and base of skull, and cervical portions such as the pharynx, larynx, esophagus and thyroid gland can be mentioned; however, cervical portions are preferably mentioned. Of them, the larynx is more preferably mentioned. Since head-and-neck tumors, in most cases, are conceivably derived from the squamous epithelium cell in term of tissue type, similarly to larynx cancer, the inhibitory substance and promoting substance of the present invention can be used for treating head-and-neck tumors other than larynx cancer and oral cancer, as a head-and-neck tumor growth inhibitor, a head-and-neck tumor metastasis inhibitor and a pharmaceutical composition for treating a head-and-neck tumor. The specific inhibitory substance and specific promoting substance of the present invention do not always have a growth inhibitory effect and a metastasis inhibitory effect on all head-and-neck tumors; however, have a growth inhibitory effect and a metastasis inhibitory effect on most of head-and-neck tumors. Therefore, by appropriately selecting an inhibitory substance and promoting substance having a growth inhibitory effect and a metastasis inhibitory effect on a target head-and-neck tumor whose growth to be inhibited, from the inhibitory substances and promoting substances of the present invention, a head-and-neck tumor growth inhibitor, head-and-neck tumor metastasis inhibitor and pharmaceutical composition for treating the head-and-neck tumor can be easily prepared.

Furthermore, the present invention also includes "a method of inhibiting growth of a head-and-neck tumor having a step of administering the inhibitory substance and/or promoting substance of the present invention to a mammal", "a method of inhibiting metastasis of a head-and-neck tumor having a step of administering the inhibitory substance and/or promoting substance of the present invention to a mammal", "a method of preventing and treating a head-and-neck tumor having a step of administering the inhibitory substance and/or promoting substance of the present invention to a mammal", "use of the inhibitory substance and/or promoting substance of the present invention in producing a head-and-neck tumor proliferation inhibitor, a head-and-neck tumor metastasis inhibitor or a pharmaceutical composition for treating a head-and-neck tumor", "use of the inhibitory substance and/or promoting substance of the present invention in inhibiting head-and-neck tumor growth or head-and-neck tumor metastasis" and "use of the inhibitory substance and/or promoting substance of the present invention in treating a head-and-neck tumor".

EXAMPLES

Reference Example 1

Analysis of Expression of microRNA in Head-and-Neck Squamous Epithelium Cancer Cell-Line Prior to performing the growth assay in Example 1 described later, expression analysis on three types of microRNAs, i.e., miR-196a, miR-133b and miR-375, was performed in the head-and-neck squamous epithelium cancer cell-line to be used in the growth assay. The expression analysis was more specifically, performed in accordance with the following method.

First, as a head-and-neck squamous epithelium cancer (one of a head-and-neck tumor) cell-line, three types of cell-lines, i.e., Ca9-22 (oral cancer cell-line), SAS (tongue cancer cell-line) and JHU-011 (larynx cancer cell-line) were prepared. Then, in accordance with the protocol attached to the mirVana miRNA Isolation Kit (manufactured by Applied Biosystems), total RNA containing a microRNA was extracted from each of the cell-lines. Using each of the total RNAs thus extracted and TaqMan (registered trademark) and MicroRNA Assays (manufactured by Applied Biosystems), expression levels of miR-196a, miR-133b and miR-375 were quantitatively determined by a real-time PCR method. The quantitative determination method was performed in accordance with the protocol attached. TaqMan probes used in the real-time PCR were probes of Part Number 4373104, 4373172 and 4373027 (manufactured by Applied Biosystems) for miR-196a, miR-133b and miR-375, respectively. As a control, total RNA derived from a non-cancer tissue of the larynx was used and expression levels of miR-196a, miR-133b and miR-375 thereof were quantitatively determined in the same manner. As a result, in Ca9-22, the expression level of miR-196a was about 65 times as high as that of the control; whereas the expression level of miR-133b was about 1/64 as low as that of the control. Furthermore, expression of miR-375 was not detected. Similarly, in SAS, the expression level of miR-196a was about 88 times as high as that of the control; whereas the expression levels of miR-133b and miR-375 were about 1/19 and about 1/148, respectively, as low as that of the control. In short, it was confirmed that miR-196a is a microRNA whose expression increases in a head-and-neck tumor; whereas miR-133b and miR-375 are microRNAs whose expression decreases in a head-and-neck tumor. The results were consistent with those in Japanese Patent Application No. 2008-243306.

Example 1

Proliferation Assay of Head-and-Neck Squamous Epithelium Cancer Cell-Line

In order to check an effect of inhibiting growth of a head-and-neck tumor with respect to an inhibitory substance of a microRNA whose expression increases in a head-and-neck tumor and a promoting substance of a microRNA whose expression decreases in a head-and-neck tumor, proliferation assay for a head-and-neck squamous epithelium cancer cell-line was performed. Assay was, more specifically, performed in accordance with the following method.

First, for miR-196a, which exhibited an increasing tendency of expression in the head-and-neck squamous epithelium cancer cell-line, an RNA (INH 196a, manufactured by Dharmacon) consisting of a complementary sequence (anti-sense sequence of miR-196a) to miR-196a RNA sequence (SEQ ID NO:6) was used as an inhibitory substance of the microRNA. Furthermore, for miR-133b and miR-375, which exhibited a decreasing tendency of expression in the head-and-neck squamous epithelium cancer cell-line, mimetic nucleic acids of the respective microRNAs, more specifically, a double-stranded RNA (MIM 133b, manufactured by Dharmacon) consisting of miR-133b RNA sequence (SEQ ID NO:9) and the complementary RNA sequence thereto, for miR-133b, and a double-stranded RNA (MIM 375, manufactured by Dharmacon) consisting of miR-375 RNA sequence (SEQ ID NO:11) and the complementary RNA sequence thereto, for miR-375, were used as the promoting substances of the microRNAs. Furthermore, as a negative control, a sequence derived from C. elegans, which is not homologous with known microRNAs of a human, a mouse and a rat were used. A negative control (INH NC, manufactured by Dharmacon) of the inhibitory substance and a negative control (MIM NC, manufactured by Dharmacon) of the mimetic substances were prepared.

Figure 1:
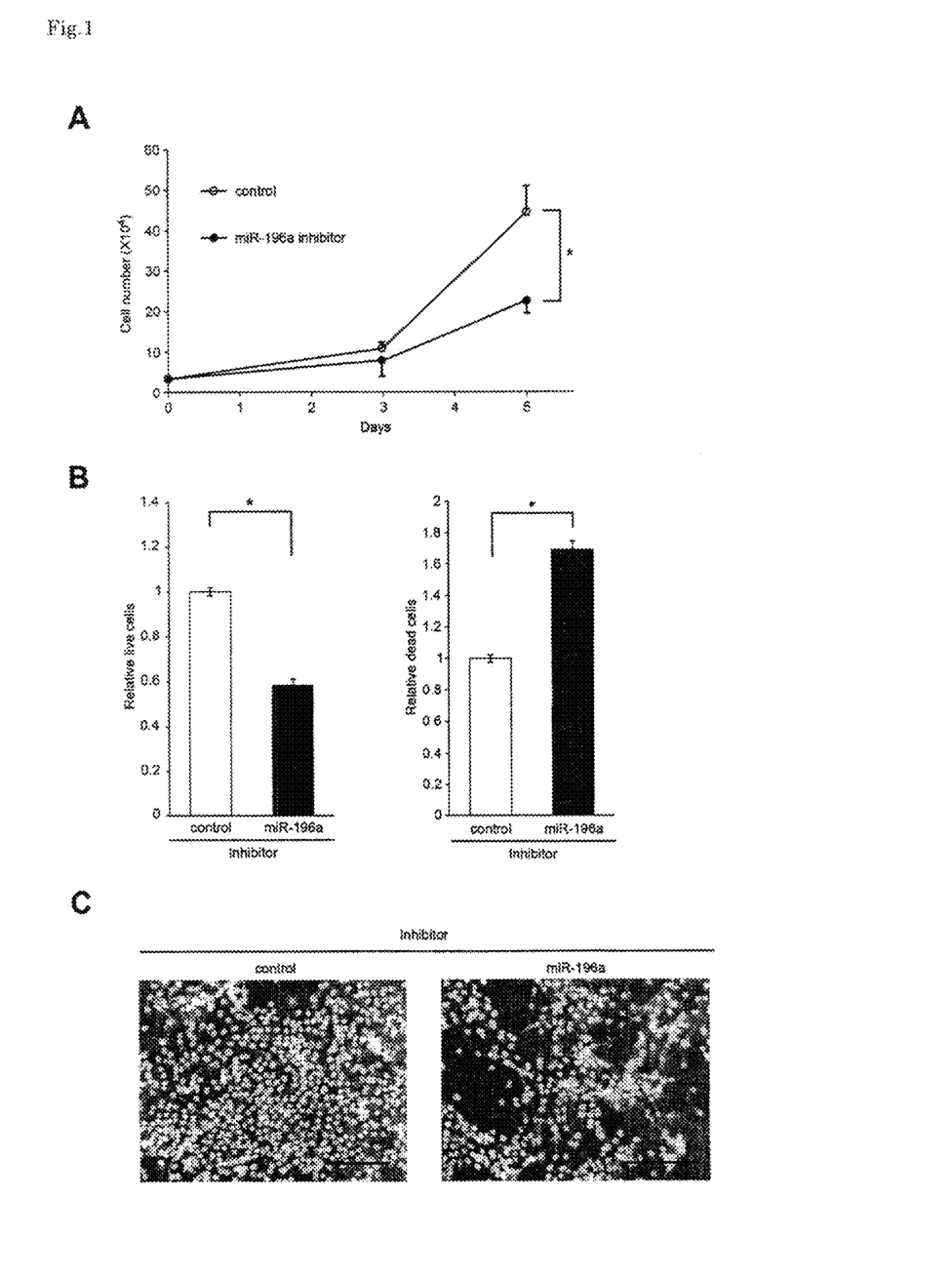

JHU-011 cells were seeded in a 24-well plate at a rate of 20,000 cells per well and the next day, transfected with INH 196a or INH NC. Thereafter, culture was performed for 5 days. At the 3rd day and 5th day of the culturing, the cells were stained with 0.4% trypan blue and the number of cells was determined by Countess (registered trademark, manufactured by Invitrogen). As a result, at the 5th day of the culturing, the number of cells was $22.67 \pm 3.06 \times 10^4$ cells/ml in the INH 196a group; whereas the number of cells was $44.33 \pm 6.66 \times 10^4$ cells/ml in the INH NC group. Proliferation of cells in the INH 196a group was significantly inhibited compared to that in the INH NC group ($p<0.01$ in the t test,) (FIG. 1A).

Next, to simultaneously evaluate the viable-cell number and the dead-cell number with respect to these, they were evaluated as relative cell numbers thereof by use of MultiTox-Fluor Multiplex Cytotoxicity Assay (manufactured by Promega KK). This assay is an approach for determining the number of viable cells and the number of dead cells in a same well by measuring the activity of two different types of proteases, i.e., a viable-cell derived protease and a dead-cell derived protease. Since the presence of the viable-cell derived protease is limited within an intact viable cell, in this assay, the viable cells can be detected by use of cell-permeable peptide substrate GF-AFC, which permeates through the membrane of a living cell and is then cleaved therein, thereby emitting a fluorescent signal in proportion to the number of viable cells. In contrast, the dead-cell derived protease, since it is released from a cell having cell membrane damaged and has activity even in a medium, can be detected by use of cell-impermeable fluorescent peptide AAF-R110 as a substrate, as a signal in proportion to the number of dead cells in accordance with a fluorescent method. To describe more specifically, JHU-011 cells were seeded in a 96-well plate at a rate of 5,000 cells per well and the next day, transfected with INH 196a or INH NC. Three days later, activity of each of the viable-cell derived protease and dead-cell derived protease was measured. Relative fluorescent signal values corresponding to viable-cell and dead-cell numbers were calculated based on an average intensity value of fluorescence derived from cells transfected with IHN NC as 1. As a result, it was confirmed in the case where INH 196a was transfected, compared to the case where INH NC was transfected, that the number of viable cells is suppressed (INH NC group: 1±0.019, INH 196a group: 0.584±0.029, p<0.01 in the t test), whereas the number of the dead cells is increased (INH NC group: 1±0.025, INH 196a group: 1.692±0.059, p<0.01 in the t test) (FIG. 1B).

Ca9-22 cells were seeded in 96-well plates at a rate of 5,000 cells and the next day, transfected with 5 μmol of INH 196a, MIM 133b, MIM 375, INH NC or MIM NC in accordance with a customary method. Thereafter, these cells were cultured for 5 days and the numbers of cells were determined. The number of cells after culturing was determined by use of WST assay, which is an indirect evaluation method using enzymatic activity of an intracellular enzyme (mitochondrial dehydrogenase) as an index. As the result of proliferation assay in Ca9-22 cells, in the case of transfection with INH 196a, the number of cells was rarely changed after culturing, compared to the case of transfection with INH NC. In contrast, in the cases of transfection with MIM 133b and MIM 375, the number of cells was likely to decrease after culturing, compared to the case of transfection with MIM NC. Particularly, in the case of transfection with MIM 375, the number of cells after culturing decreased as large as by 42.1% (p<0.01 in the t test), compared to the case of transfection with MIM NC.

Furthermore, SAS cells were subjected to the same proliferation assay. As a result, in the case of transfection with INH 196a, the number of cells after culturing rarely changed, compared to the case of transfection with INH NC. Furthermore, in the case of transfection with MIM 375, the number of cells after culturing rarely changed, compared to the case of transfection with MIM NC; whereas in the case of transfection with MIM 133b, the number of cells after culturing decreased as large as by 35.1% (p<0.01 in the t test), compared to the case of transfection with MIM NC.

Furthermore, JHU-011 cells were subjected to the same proliferation assay. As a result, in the case of transfection with INH 196a, the number of cells after culturing decreased as large as by 20.0%, compared to the case of transfection with INH NC. Furthermore, in the cases of transfection with MIM 133b and MIM 375, the number of cells after culturing was likely to decrease, compared to the case of transfection with MIM NC; in particular, in the case of transfection with MIM 375, the number of cells after culturing decreased as large as by 29.2%, compared to the case of transfection with MIM NC.

Figure 2:
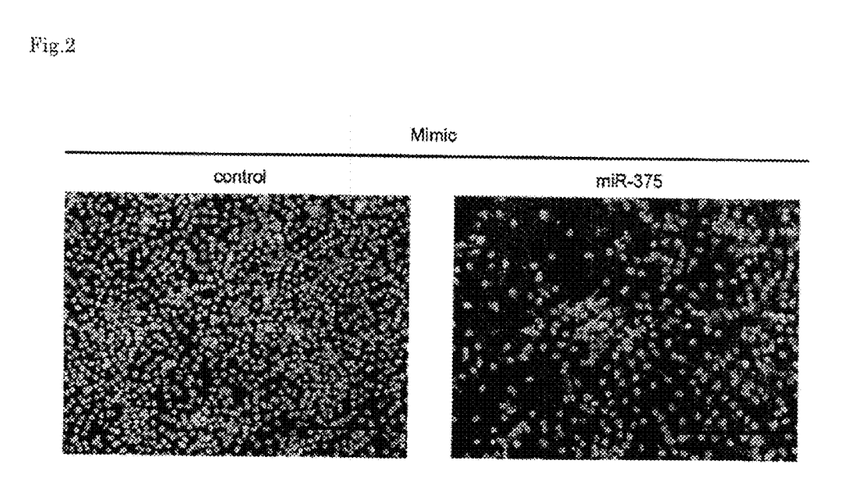
FIG. 2
FIG. 2, the left panel: A fluorescence micrograph showing the state of JHU-011 cells, which were transfected with MIM NC (negative control), cultured for 5 days and subjected to Hoechst staining.

The cell proliferation inhibitory effect on the JHU-011 cells was also confirmed by another method. For this, the cells were transfected with INH 196a, MIM 375, INH NC, and MIM NC, subjected to Hoechst staining and observed by a fluorescent microscope. Hoechst staining is a staining method using a fluorescent dye, Hoechst, which binds to a double-stranded DNA of a nucleus and emits blue fluorescence when it is excited by UV ray wavelength. In this mechanism, the number of cells can be visually observed by eye. In this respect, the accuracy of this method is higher than the WST assay which indirectly evaluating the number of cells. According to the Hoechst staining, the cell proliferation inhibitory effects of 3-day later (FIG. 1C) and 5-day later (FIG. 2) in the case of transfection with INH 196a or MIM 375, coincided with the cell proliferation inhibitory effect calculated from the results of the WST assay.

Then, quantification of the cell proliferation inhibitory effect was performed by the approach as follows. First, Ca9-22 cells, SAS cells, JHU-011 cells as well as FaDu cells of squamous epithelium cancer cell-line (lower pharynx cancer cell-line) were cultured on slide glasses (BD BioCoat® manufactured by BD Falcon). After 24 hours, the cells were transfected with INH 196a, MIM 133b, MIM 375, or controls, i.e., INH NC and MIM NC by using Lipofectamine® 2000 (manufactured by Invitrogen). Thereafter, the cells were cultured for 3 days and nuclear staining was performed by Hoechst 33258. A staining-region of a cell image under a microscope was measured by image analysis software (Image-Pro Plus®). As a result, compared to the case of Ca9-22 cells transfected with MIM NC, the number of the cells transfected with MIM 375 decreased by 40.3%. Furthermore, compared to the case of SAS cells transfected with MIM NC, the number of the cells transfected with MIM 133b decreased by 23.1%. Furthermore, compared to the cases of JHU-011 cells and FaDu cells transfected with controls, it was confirmed that the number of cells decreases in all transfection cases as follows: INH 196a (JHU-011 cells: 38.5% decrease in cell number, FaDu cells: 53.6% decrease in cell number), MIM 133b (JHU-011 cells: 38.8% decrease in cell number, FaDu cells: 27.3% decrease in cell number), MIM 375 (JHU-011 cells: 49.9% decrease in cell number, FaDu cells: 57.9% decrease in cell number).

From these results in the foregoing, it was demonstrated that an inhibitory substance of a microRNA whose expression increases in a head-and-neck tumor and a promoting substance of a microRNA whose expression decreases in a head-and-neck tumor have a growth inhibitory effect on a head-and-neck tumor.

Example 2

In-Vivo Growth Assay Using Head-and-Neck Tumor Model Mouse

To check as to whether an inhibitory substance of a microRNA whose expression increases in a head-and-neck tumor has the growth inhibitory effect on a head-and-neck tumor even in vivo, in-vivo growth assay was performed. More specifically, the following method was employed.

Figure 3:
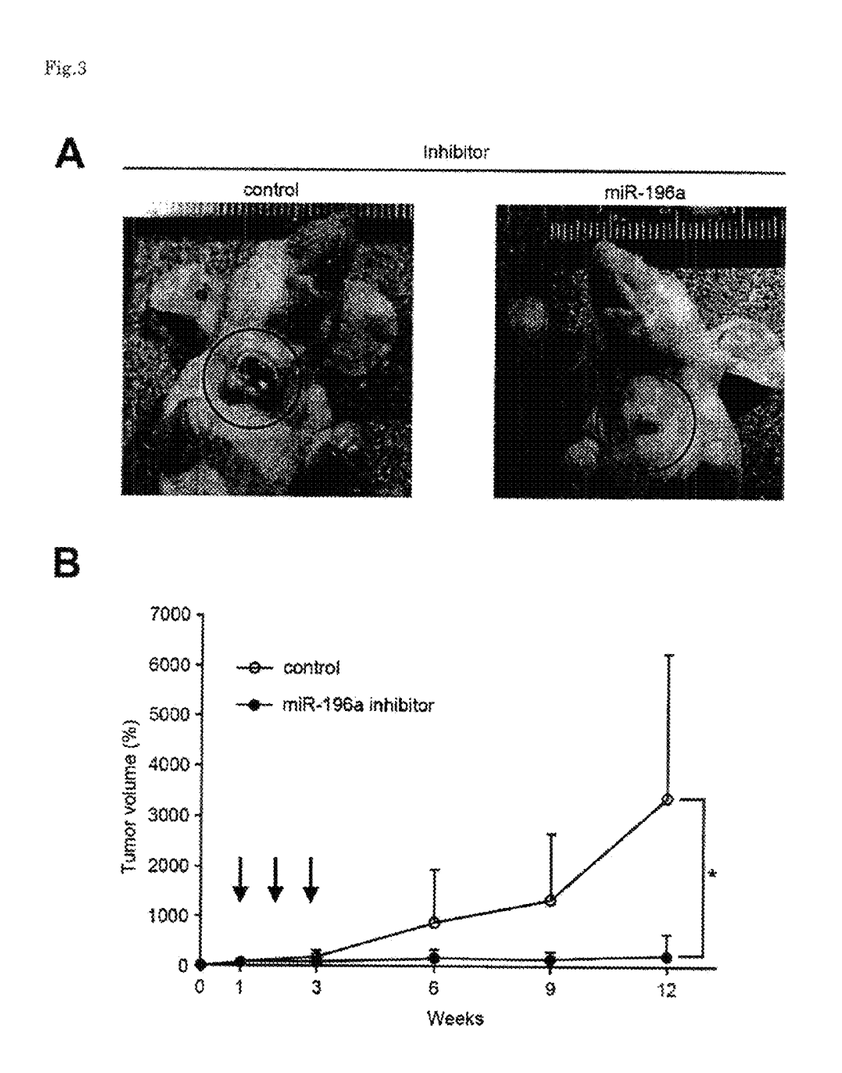

To the cervical region of each of ten 6-week-old nude mice, xenogenic grafting of larynx cancer-derived human squamous epithelium cancer cells, JHU-011 ($5 \times 10^6$ cells) was performed to prepare head-and-neck tumor model mice. At the 7th day after grafting, it was confirmed that a tumor was developed in the cervical region of the head-and-neck tumor model mice and then these head-and-neck tumor model mice were divided into two groups. To one of the groups, miR-196a inhibitor was administered and treated as INH 196a administration group (n=5) as mentioned above. To the other group, an inhibitor (negative control) was administered and treated as a negative control administration group (n=5) as mentioned above. At the 7th day (D7), 13th day (D13) and 19th day (D19) after grafting with JHU-011, a mixture of 1 nmol of INH 196a (0.1 ml of 10 μM Dharmacon microRNA) and 0.1 ml of atelocollagen (AteloGene (registered trademark) manufactured by Koken Co., Ltd.) was administered to the INH 196a administration group, and a mixture of 1 nmol of an inhibitor negative control (0.1 ml of 10 μM Dharmacon microRNA) and 0.1 ml of atelocollagen (AteloGene (registered trademark) manufactured by Koken Co., Ltd.) was administered to the negative control administration group, more specifically, both groups administered locally to the periphery of a tumor. The sizes (length/width/height) of tumors of all head-and-neck tumor model mice were measured in 1 week (1 W), 3 weeks (3 W), 6 weeks (6 W), 9 weeks (9 W), 12 weeks (12 W) after grafting. The resultant length value, width value and height value were multiplied to obtain a volume value and both groups were compared based on a volume ratio. The tumors observed in 9 weeks later (9 W) are shown in FIG. 3A (the left: the negative control administration group, the right: the INH 196a administration group). Furthermore, FIG. 3B shows a change of an average relative tumor volume (%) of each group based on the average tumor volume of the group in 1 week later (1 W) as 100%. From the above, it is clearly shown that an increase of a tumor in the head-and-neck tumor model mice can be remarkably (FIG. 3A) and significantly (* p<0.05) (FIG. 3B) inhibited by administration of an inhibitory substance of miR-196a, and demonstrated that the growth inhibitory effect on a head-and-neck tumor can be obtained even in vivo.

Example 3

Pathological Observation on Tumor Tissue in Head-and-Neck Tumor Model Mouse

Figure 4:
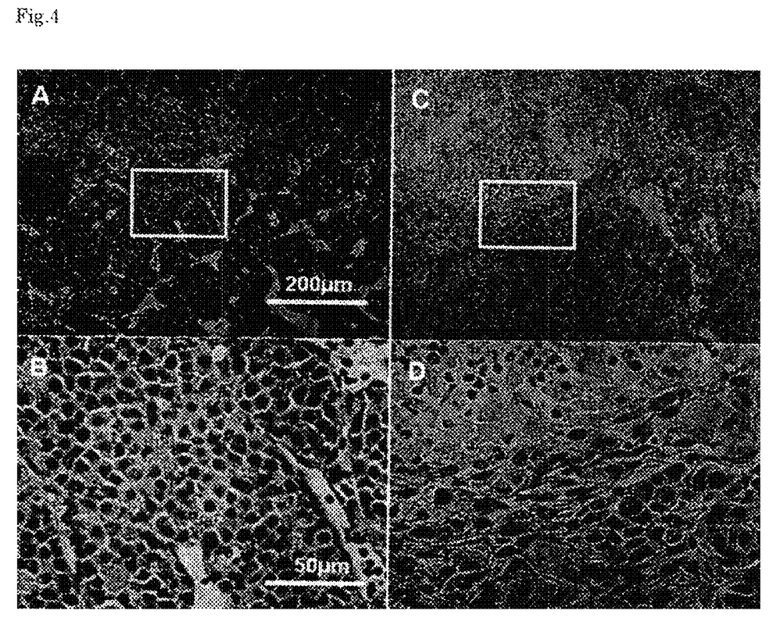

In the in-vivo growth assay of Example 2, tumors were excised out from the tumor tissues in head-and-neck tumor model mice of both groups in 3 months after grafting, fixed with 10% formalin fixation and embedded in paraffin to obtain tissue preparations. The tissue preparations were subjected to hematoxylin/eosin staining (HE staining) and tissue morphology was observed. The results are shown in FIGS. 4A to D. FIG. 4A shows the observation result of a tumor tissue-preparation of the INH 196a administration group and FIG. 4B is a partly enlarged view of the tissue preparation (a portion surrounded by the square in FIG. 4A). FIG. 4C shows the observation result of a tumor tissue-preparation of the negative control administration group and FIG. 4D is a partly enlarged view of the tissue preparation (a portion surrounded by the square in FIG. 4C). In the negative control administration group, proliferation of cancer cells (oat-form cells) partly with necrosis was observed (FIGS. 4C and D); whereas in the INH 196a administration group, an increase of histiocytes was observed within the tumor; however the presence of cancer cells was not confirmed (FIGS. 4A and B). From the results, it was also pathologically supported that administration of an inhibitory substance of miR-196a has a growth inhibitory effect on a head-and-neck tumor.

Example 4

Figure 5:
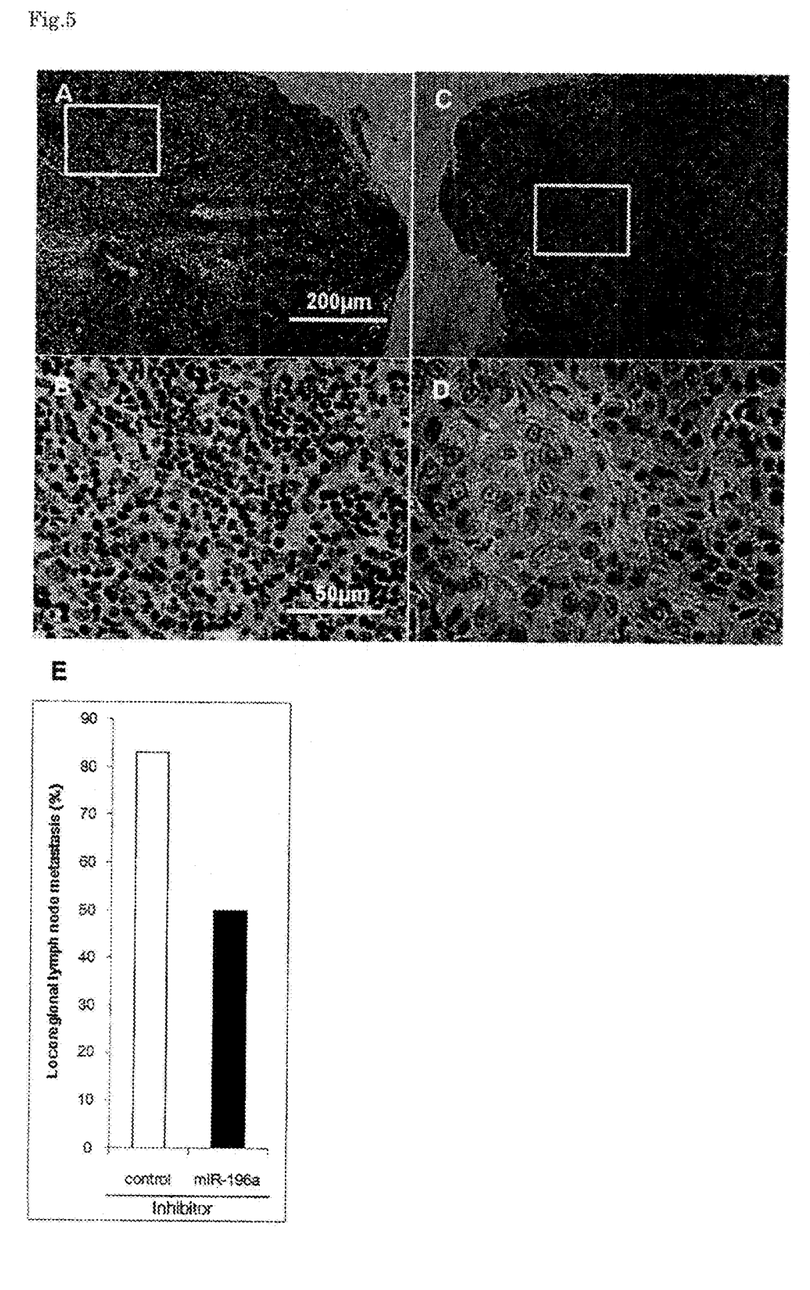
FIGS. 5A to D: Photographs showing the results of tissue slices, which were prepared from the cervical lymph-node tissues of both head-and-neck tumor model mouse groups (3 months after grafting) in the experiment of FIG. 3 and subjected to hematoxylin/eosin staining (HE staining).
FIG. 5E: A graph showing the percentage of metastasis in the cervical lymph node, which was excised out from both head-and-neck tumor model mouse groups (3 months after grafting) in the experiment of FIG. 3. Note that the left bar graph shows the results of the INH NC administration group; whereas the right bar graph shows the results of the INH 196a administration group.

Pathological Observation on Lymph Node Tissue in Head-and-Neck Tumor Model Mouse In the in-vivo growth assay of Example 2, cervical lymph nodes were excised out from head-and-neck tumor model mice of both groups in 3 months after grafting, fixed with 10% formalin and embedded in paraffin to obtain tissue preparations. The tissue preparations were subjected to hematoxylin/eosin staining (HE staining) and tissue morphology was observed. The results are shown in FIGS. 5A to D. FIG. 5A shows the result of a tissue preparation of the cervical lymph node of the INH 196a administration group and FIG. 5B is a partly enlarged view of the tissue preparation (a portion surrounded by the square in FIG. 5A). FIG. 5C shows the result of the tissue preparation of the cervical lymph node of the negative control administration group and FIG. 5D is a partly enlarged view of the tissue preparation (a portion surrounded by the square in FIG. 5C). In the negative control administration group, cancer cells (oat-form cells) proliferated and metastasis of cancer was observed (FIGS. 5C and D); whereas in the INH 196a administration group, the presence of cancer cells was not confirmed and no metastasis of cancer was observed (FIGS. 5A and B). Furthermore, two mice were selected from each of both tumor model mouse groups and a plurality of cervical lymph nodes were excised out from them and then the presence or absence of metastasis of cancer was histologically checked. As a result, metastasis was observed in 83% of the cervical lymph node (locoregional lymph node) in the negative control administration group; whereas metastasis was observed only in 50% of the lymph node in the INH 196a administration group (FIG. 5E). From the above results, it was pathologically demonstrated that not only growth of head-and-neck tumor but also metastasis to the lymph node can be inhibited by administration of an inhibitory substance of miR-196a.

INDUSTRIAL APPLICABILITY

The present invention is particularly useful in the field of head-and-neck tumor therapy by inhibiting growth of tumor and metastasis.

The invention claimed is:

1. A head-and-neck tumor proliferation inhibitor comprising an inhibitory substance of miR-196a, wherein the inhibitory substance of miR-196a is an antisense nucleic acid of miR-196a and wherein expression of miR-196a is increased in a head-and-neck tumor.

2. A head-and-neck tumor metastasis inhibitor comprising an inhibitory substance of miR-196a, wherein the inhibitory substance of miR-196a is an antisense nucleic acid of miR-196a and wherein expression miR-196a is increased in a head-and-neck tumor.

* * * * *

SEQUENCE LISTING

```
<160> NUMBER OF SEQ ID NOS: 11

<210> SEQ ID NO 1
<211> LENGTH: 21
<212> TYPE: RNA
<213> ORGANISM: Homo sapiens

<400> SEQUENCE: 1
gcaguccaug ggcauauaca c                                                 21

<210> SEQ ID NO 2
<211> LENGTH: 22
<212> TYPE: RNA
<213> ORGANISM: Homo sapiens

<400> SEQUENCE: 2
uaugugccuu uggacuacau cg                                                22
```

-continued

```
<210> SEQ ID NO 3
<211> LENGTH: 22
<212> TYPE: RNA
<213> ORGANISM: Homo sapiens

<400> SEQUENCE: 3
cagugcaaug augaaagggc au                                                  22

<210> SEQ ID NO 4
<211> LENGTH: 21
<212> TYPE: RNA
<213> ORGANISM: Homo sapiens

<400> SEQUENCE: 4
acucuuuccc uguugcacua c                                                   21

<210> SEQ ID NO 5
<211> LENGTH: 24
<212> TYPE: RNA
<213> ORGANISM: Homo sapiens

<400> SEQUENCE: 5
gauugcucug cgugcggaau cgac                                                24

<210> SEQ ID NO 6
<211> LENGTH: 21
<212> TYPE: RNA
<213> ORGANISM: Homo sapiens

<400> SEQUENCE: 6
uagguaguuu cauguuguug g                                                   21

<210> SEQ ID NO 7
<211> LENGTH: 22
<212> TYPE: RNA
<213> ORGANISM: Homo sapiens

<400> SEQUENCE: 7
uagcuuauca gacugauguu ga                                                  22

<210> SEQ ID NO 8
<211> LENGTH: 21
<212> TYPE: RNA
<213> ORGANISM: Homo sapiens

<400> SEQUENCE: 8
ggcaagaugc uggcauagcu g                                                   21

<210> SEQ ID NO 9
<211> LENGTH: 21
<212> TYPE: RNA
<213> ORGANISM: Homo sapiens

<400> SEQUENCE: 9 uuggucccu ucaaccagcu a                                                    21

<210> SEQ ID NO 10
<211> LENGTH: 23
<212> TYPE: RNA
<213> ORGANISM: Homo sapiens

<400> SEQUENCE: 10
guccaguuuu cccaggaauc ccu                                                 23
```

```
<210> SEQ ID NO 11
<211> LENGTH: 22
<212> TYPE: RNA
<213> ORGANISM: Homo sapiens

<400> SEQUENCE: 11
uuuguucguu cggcucgcgu ga                                              22
```